United States Patent [19]

Steinhauer et al.

[11] Patent Number: 4,805,638
[45] Date of Patent: Feb. 21, 1989

[54] APPARATUS FOR PHOTOGRAMMETRICALLY MEASURING THE HUMAN HEAD

[75] Inventors: Eric Steinhauer, La Canada, Calif.; Karl-Heinz Lange, Bunde, Fed. Rep. of Germany

[73] Assignee: Eyemetrics - Systems AG, Chur, Switzerland

[21] Appl. No.: 933,580

[22] Filed: Nov. 21, 1986

[30] Foreign Application Priority Data

Dec. 23, 1985 [DE] Fed. Rep. of Germany ....... 3545875

[51] Int. Cl.$^4$ ............................................... A61B 5/10
[52] U.S. Cl. .................................... 128/774; 128/777; 33/512; 354/77
[58] Field of Search ...................... 128/774, 782, 777; 33/512, 515, 511; 354/77, 80, 81

[56] References Cited

U.S. PATENT DOCUMENTS

| | | | |
|---|---|---|---|
| 1,564,339 | 12/1925 | Fraser et al. ........................... | 33/515 |
| 2,339,657 | 1/1944 | Smith . | |
| 2,780,004 | 2/1957 | Rosenbaum . | |
| 4,135,498 | 1/1979 | McGee ................................ | 128/774 |
| 4,538,353 | 9/1985 | Gardner ............................. | 33/515 X |
| 4,567,671 | 2/1986 | Yalk ...................................... | 33/512 |
| 4,604,807 | 8/1986 | Bock et al. .......................... | 33/515 X |
| 4,662,079 | 5/1987 | Graf et al. .......................... | 33/515 X |

FOREIGN PATENT DOCUMENTS

| | | | |
|---|---|---|---|
| 0140681 | 5/1985 | European Pat. Off. ............ | 128/774 |
| 2491323 | 4/1982 | France ................................. | 128/774 |
| 0923522 | 5/1982 | U.S.S.R. .............................. | 128/774 |
| 2159943 | 12/1985 | United Kingdom ................ | 128/774 |

OTHER PUBLICATIONS

Proceedings of the Society of Photo-Optical Instrumentation Engineers, SPIE, Band 166, 1978, Seiten 235-243; G. Akerskog et al, "Children's Glasses".

Primary Examiner—Kyle L. Howell
Assistant Examiner—Angela D. Sykes
Attorney, Agent, or Firm—Roth & Goldman

[57] ABSTRACT

The present device for the photogrammetrical measurement of the human head, especially of the middle region of the face with the eye sockets, the nose, the cheek bones and the brows, is comprised of a projector for projecting a pattern image onto the face and two cameras which can simultaneously take two pictures from two different directions of the face and head with the pattern image projected on it. The two cameras and the projector are supported by an apparatus carrier, which can be moved in a vertical direction relative to a base permanently connected to the device and in at least one horizontal direction. This minimum of one direction coincides with the optical axes of the cameras. The device will facilitate bringing both the projector and the cameras on the one hand and the human head on the other into the required relative position to one another as necessary to take the pictures.

26 Claims, 4 Drawing Sheets

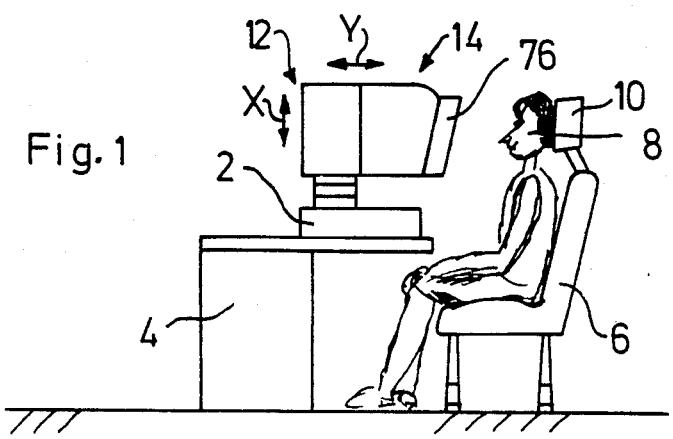
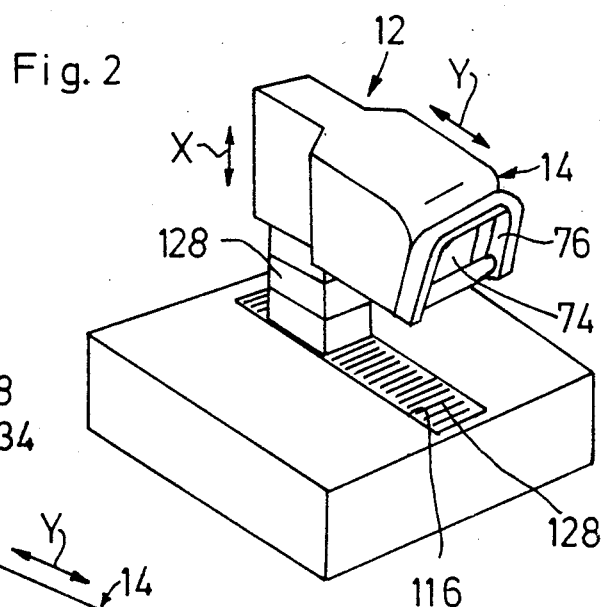
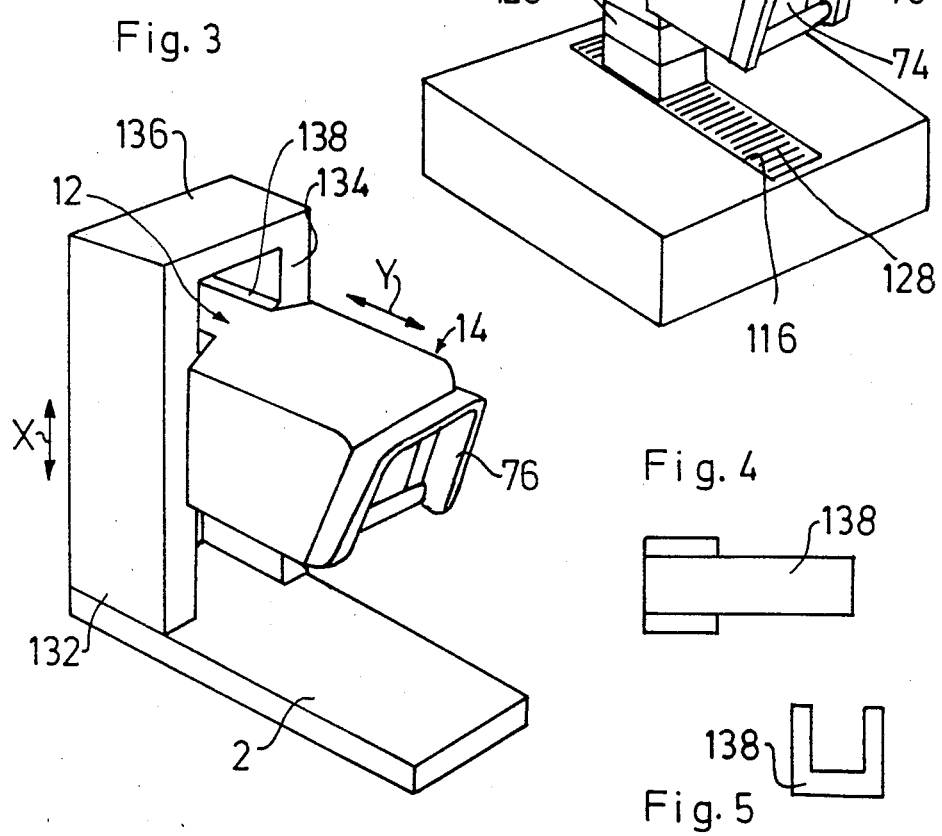
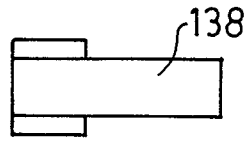
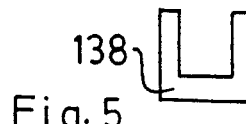

APPARATUS FOR PHOTOGRAMMETRICALLY MEASURING THE HUMAN HEAD

FIELD OF THE INVENTION

The present invention relates to a device for photogrammetrically measuring the human head.

PRIOR ART

Known in the art is a device (SPIE Vol. 166 Applications of Human Biostereometrices, NATO, 1978, pp. 235-243) by means of which the front side of the head of a human being, i.e. essentially his face, his temple areas and the ears can be photographically recorded while an appropriate pattern form is projected onto the face. In this process two pictures are made simultaneously from two different directions, the evaluation of which makes it possible to measure the three-dimensional geometry of the photographed area of the head. This device known in the art serves the purpose of measuring average courses of nose profiles between the eyes, average intervals of the root of the nose from the base of the ear in side view, average intervals between the bases of the ear and so forth in order to determine on the basis of this data the dimensions of spectacle frames.

A condition for an exact photogrammetrical measurement of the type described in the above is for the object, i.e. the front side of the head to be located in a definite, known object position relative to the camera direction and to the projector, and thus object distance. In this instance known in the art this is accomplished by directing the camera equipment and the projector on the object level and setting the object distance and by having the person whose head is being measured situated in such a way that his head is located in the object level as exactly as possible. This process demands a willingness to cooperate on the part of the person and also relatively a great deal of time. In addition, it has been determined that fixing the head sometimes causes a tense and unnatural posture to be assumed that in turn is reflected in the expression on the face and that can possibly cause distortions of the face, which stand in the way of a precise measurement.

SUMMARY OF THE INVENTION

The present invention is based on the objective of designing the device of this genre in such a manner that it will be possible to conduct photogrammetrical measurements with as few exertions as possible on the part of the person whose head is to be measured and the person operating the device. In particular, it is intended both that the measurement should be made quickly and that a relaxed, natural facial expression should be achieved.

In the device in accordance with the present invention an apparatus carrier which carries both the camera equipment and the projector and, together with these, forms a unit described in the following as an optical head. This optical head can be moved in a vertical direction relative to the base fixed with respect to the device and also horizontally in at least one direction, whereby this one direction coincides essentially with the optical axis of the camera equipment. The design in accordance with the present invention makes it possible to proceed in the photogrammetry in such a manner that the person whose head is to be measured takes a seat in a seating facility and then assumes a comfortable sitting posture with the upper body held essentially erect and with the head held straight. With this positioning the person need not be reminded to keep the head at a certain level, but instead can and should assume a comfortable and relaxed posture, whereby the level and location in space in and at which the upper region of the head of the person is situated is adjusted according to the individual characteristics of the person in question. After the person has assumed the position described above, the optical head is then moved by virtue of the mobility furnished in accordance with the present invention into such a height and at such a interval to the face that the front region of the head and face will be located in the object level set for the camera facility and the projector and the viewing range of the camera equipment. When the optical head has reached this position, at least one photogrammetrical picture can be taken. In this process it is no longer demanded of the person whose head is being measured to do any more than sit comfortably upright. The operator need solely move the optical head in the manner described and must neither fix the subject's head in place manually nor cause the person through instructions to move his head in a certain prescribed position.

The camera equipment will preferably be capable of taking pictures simultaneously from two different directions, which is possible, for example, with two cameras the fields of vision of which at least overlap. Each of these two cameras has its own optical axis; in this case an axis extending in the middle between the optical axes of the two cameras can, for example, be regarded as the optical axis of the camera facility. The essential mobility furnished in the device in accordance with the present invention is available in the horizontal direction when the optical head of the device is adjustably moveable toward the human head to be measured and away from t while the human head is situated in the viewing range of the camera equipment. Mobility in the one horizontal direction is also furnished when a transverse component is superimposed on the motion in the horizontal direction, i.e. when, for example, a movement is made forward (toward the human head) simultaneously or to the rear.

In a preferred embodiment of the present invention provision can be made for the apparatus carrier to be movable in a second horizontal direction essentially perpendicular to the first horizontal direction. This will make it easier to bring the face into the prescribed viewing range and the prescribed object level of the camera facility by moving the optical head even when the person is sitting markedly to the side on the seating facility.

In a further embodiment of the present invention electrical motor driving equipment is provided for the movements of the apparatus carrier and optical head into the directions of motion it is capable of performing.

In addition to the above described movability of the apparatus carrier and optical head, provision can be made for the idealized picture projected from the projector to be finely adjusted with the optical head at rest, which can be achieved by pivoting the projector and turning the diapositive in the project that holds the copy of the pattern image. By means of this design it will be possible in a simple manner to bring the pattern image into a certain spatial coordination with certain features of the face, thus making is easier to evaluate both of the pictures.

In a further embodiment of the device provision can be made for a hood with two side walls, a bottom wall, and upper wall and a front wall to be affixed on the apparatus carrier, whereby the front wall is equipped with an aperture for the head and which has approximately the same distance from the apparatus carrier that the head has during measurement from the apparatus carrier, and whereby the hood darkens the space between the camera facility and the projector on the one hand and the front wall on the other. Any interference with the measurements from intrusive light is prevented by such a hood. In addition to this, a distance measuring device, a device for illuminating the eye socket and a calibrating object will preferably be installed in the hood. The distance measuring device, which will preferably be designed with two light barriers, measures the condition for the fact that the head to be measured takes the nominal interval from the camera facility, i.e. is located in the prescribed, definite object level onto which the camera facility and the projector are set. The eye socket illumination device has shown itself to be useful for preventing too heavy a shading of the eye sockets and the low degree of contrast caused by this in pictures taken in the region of the eye sockets. Finally, the calibrating object is of especial advantage, and will be movable preferably between a rest position and a calibrating position, and is permanently connected directly to the apparatus carrier and the optical head by virtue of its situation in the hood. This guarantees both that when needed the calibrating object will be readily available at any time and that in calibrating position it will assume a position reproducible in a high degree in relation to the camera equipment.

The above described device is especially suitable for measuring the human head in the region of the nose, the eye sockets, the brows, the cheek bones, the temples and the ears for the purpose of obtaining precise data for producing spectacles. If the device in accordance with the present invention is employed for this purpose, it will be of advantage to take measurements of the areas between the two ears and the temples of the head in sufficient measure at the same time as the measurements are taken of the face in the above mentioned area. In a preferred embodiment of the present invention thus two ear scanners are provided which can be applied respectively to the area between one ear and the temple of the head and are fitted with markings that are visible simultaneously from the front side when the ear scanner is applied, as well as a parallel guiding device for each of the ear scanners to make it possible for each ear scanner to be shifted parallel in vertical position in the first horizontal position. In a further embodiment of the present invention the two parallel guiding devices of the ear scanners are likewise situated in the hood and attached to this.

BRIEF DESCRIPTION OF THE DRAWINGS

FIG. 1 a lateral view of a preferred embodiment of the device;

FIG. 2 a view in perspective of the essential parts of the device according to FIG. 1;

FIG. 3 a second embodiment of the device similar to the view in FIG. 2;

FIG. 4 a top-view of a sliding carriage of the embodiment according to FIG. 3;

FIG. 5 a lateral view of the sliding carriage according to FIG. 4 from the left as seen in FIG. 4;

FIG. 11 a side view of the embodiment according to FIG. 10; and

FIG. 12 a side view of the third embodiment of the device from the right as seen in FIG. 11.

DESCRIPTION OF THE PREFERRED EMBODIMENTS

Figure 6:
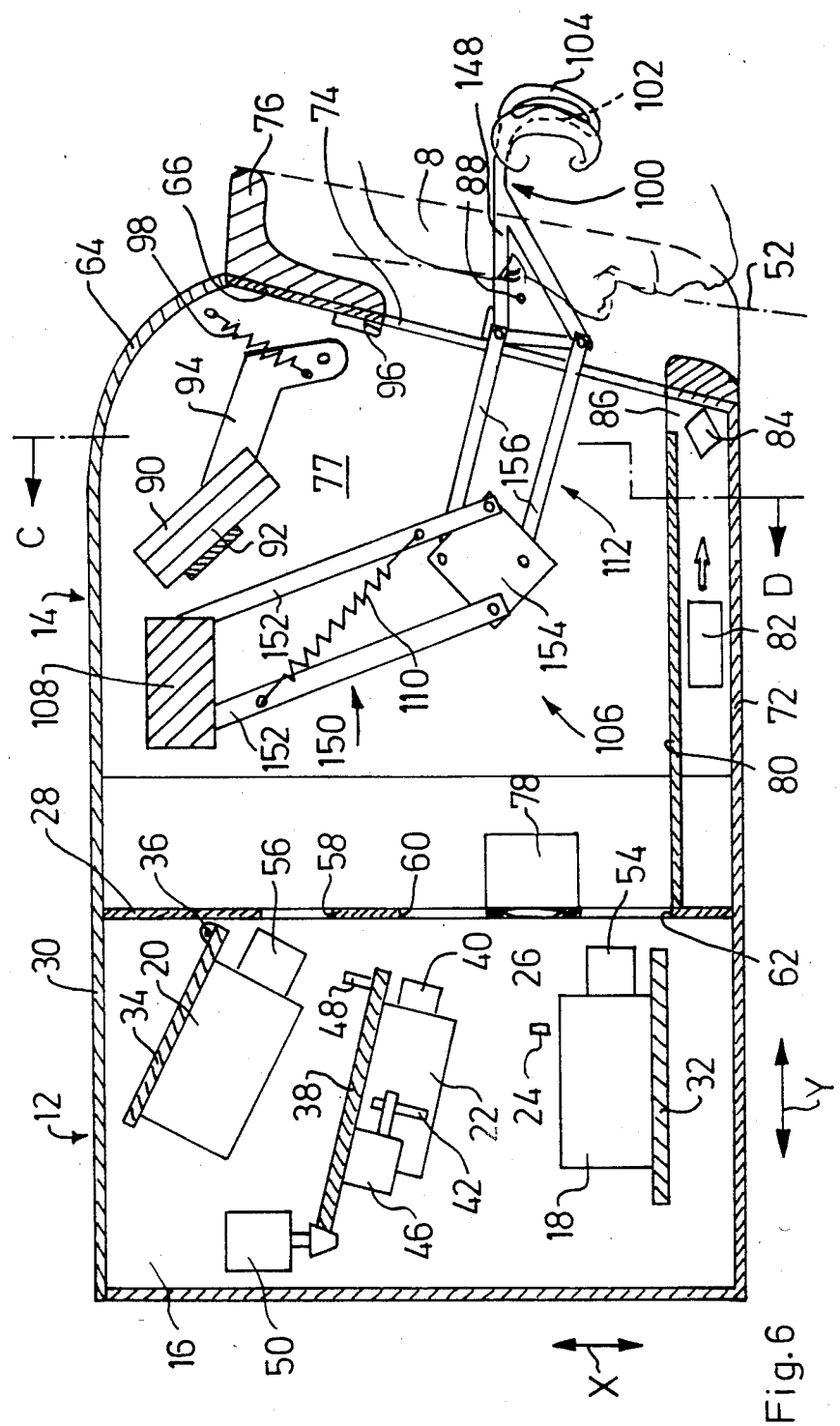
FIG. 6 a section in enlargement along A - B in FIG. 8 through an optical head and a camera unit permanently attached to it in the embodiment according to FIGS. 1 and 2.

The same reference numerals in the figures refer to identical or analagous parts or elements.

The preferred embodiment shown in FIGS. 1, 2, 6, 7 and 8 of the device is comprised of a box-shaped base 2, located on a table 4. In front of the base 2 and the table 4 is a seating facility 6 in the shape of an upright-leaning chair in which the person can be seated, the head 8 of whom is to be measured photogrammetrically. The seating facility 6 supports an adjustable head support 10 at the upper end of its backrest.

Above the base 2 firmly attached to the device an optical head 12 and a chamber unit 14 are situated. The optical head 12 and the chamber unit 14 are permanently attached to one another and are jointly movable in a vertical direction relative to the base 2 and in a horizontal direction, as is shown in FIGS. 1 and 2 by the double arrow X for the vertical direction and by the double arrow Y for the horizontal direction. In the following the optical head 12 and the chamber unit 14 will first be described in greater detail with reference to the FIGS. 6 through 8.

The optical head 12 is comprised of several optical instruments as well as an apparatus carrier 16, which supports the optical instruments. The optical instruments include a lower camera 18, in the form of a video camera, an upper camera 20 in the form of a video camera, a projector 22, an observation object 24 and a lens arrangement 26 aligned with the latter. The apparatus carrier 16 in the embodiment illustrated comprises a self-supporting, rigid case with a front wall 28 at the right as seen in FIG. 6, an upper wall 30, together with other walls not shown in the drawing and with mountings for the optical instruments. These mountings consist of a first mounting 32, which is connected to the remainder of the apparatus carrier 16 in a manner not shown in the illustration and on which the lower camera 18 is attached so as to be dismountable and interchangeable. In addition, belonging to the mountings is a second mounting 34, on which the upper camera 20 is attached so as to be dismountable and interchangeable. The second mounting 34 is fitted on the remainder of the apparatus carrier 16 in such a manner that this mounting, and thus the upper camera 20 supported by it, can be pivoted around a bearing point 36, and can also be rotated around an axis extending vertically in the drawing plane of FIG. 6 to the optical axis of the upper camera 20. This swivel and rotational feature permits alignment of the optical axis of the upper camera 20 in such a manner that the viewing range of the upper camera 20 overlaps with the viewing range of the lower camera 18 to the extent that is desired and necessary. When the proper setting of the upper camera 20 is found, the second mounting 34 is fixed in place In the embodiment described here the two cameras 18 and 20 comprise the camera facility of this device. Although cameras which record pictures on film can be considered, video cameras are to be preferred, and specifically digital cameras especially, which allow for real-time processing and handling. Video cameras suitable for this are those in CCD circuit technology, CID circuit technology and CMOS circuit technology. Digital video cameras have been especially demonstrated as superior with respect to the precision of the photogrammetrical evaluation of the camera signals.

Although in the embodiment shown here two cameras form the camera facility, the camera equipment can consist of solely one camera or even three cameras. In the case of three cameras which make three pictures, one definite object point in addition will be recognizable and identifiable if this is only recognizable in two of the pictures, but not in the third. If the camera facility is constituted of only one camera, this camera can be equipped with a device which simultaneously produces two pictures of the object in the picture level of the camera, and specifically two pictures that differ from one another by varying directions of observation. Such a device can be fashioned, for example, by means of a mirror arrangement. And finally, it is also possible to operate with only one camera and to take only one picture, whereby the computation of the photogrammetrical evaluation is more laborious, but still is not impossible.

Figure 9:
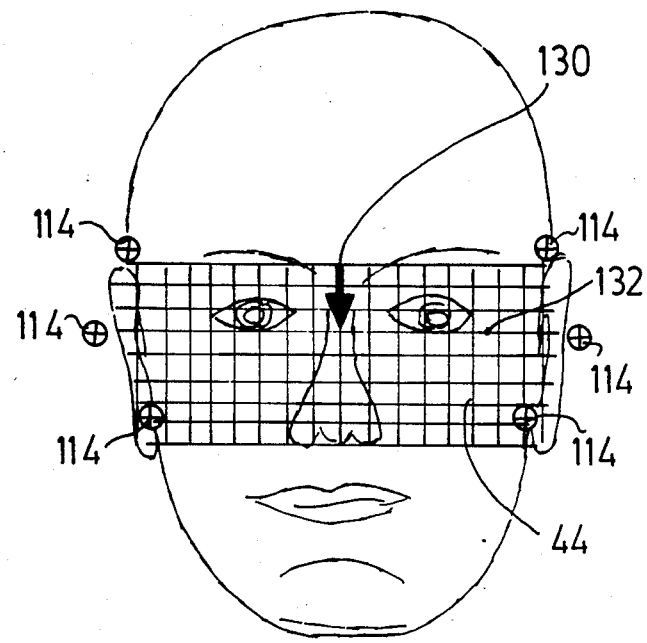
FIG. 9 a front view of a human head during measurement with observation made along the optical axis of a projector of the device.

A third mounting 38 is also part of the mountings of the apparatus carrier 16 and to this is attached the projector 22 in such a manner as to be dismountable and interchangeable. The projector 22 has an objective 40 and holds a diapositive 42 which for its part carries the copy for a grid pattern image 44 to be projected by means of the projector 22, which picture is schematically depicted in FIG. 9 and which, for example, can take the form of a rectangular grid. A placing drive 46 is fitted on the mounting 38 for the projector 22, by means of which drive the diapositive 42 in the projector 22 can be rotated around the optical axis of the latter in a manner not described in more detail, so that in this manner even the grid pattern image 44 can be rotated around an axis vertical to the drawing plane of FIG. 9 as well.

The mounting 38 for the projector 22 can be pivoted around an axis 48 found in the drawing plane of FIG. 6 and extending through the principal plane of the objective 40. The pivoting is accomplished by means of a second placing drive 50, which acts on the mounting 38 in a manner only schematically depicted. By pivoting the projector 22 by means of the placing drive 50 the idealized picture 44 projected from the projector 22 can be shifted laterally, i.e. to the right or to the left as seen in FIG. 9.

At a certain interval from the optical head 12 is located a working plane 52, which is shown in FIG. 6 in a dash-dot line. The measuring object to be examined, viz. the front region of the head 8, should be located in this working plane 52 in order for the measuring object to be situated in the depth of focus range of the two cameras 18 and 20, as well as of the projector 22. Accordingly, both the objective 40 of the projector 22 and the objectives 54 and 56 of the cameras 18 and 20 are focused on this working plane 52. In addition, the measuring object should occupy a certain place in the working plane 52, so that it is located approximately coaxially in the viewing range of the two cameras 18 and 20. This position of the measuring object in the working plane 52 is termed the measuring position. The optical axes of the two objectives 56 and 54 are aligned in such a manner that the measuring object located in the measuring position can be sharply recorded by means of the two cameras 18 and 20 from two directions differing from one another. The state of focusing of the two cameras 18 and 20 as well as of the projector 22 and the alignment of the two cameras 18 and 20 are not altered during operation, so that by virtue of the set focusing states and alignments the site of the working plane 52 and the requisite measuring position of the head 8 remain constant relative to the optical head 12. One of the special features of the device described here is that fact that it is not the human head 8 that actively moves into the measuring position but the optical head 12— together with the elements permanently attached to it - that is shifted in a vertical direction and horizontally until the human head 8 comes into the measuring position. For this purpose the horizontal shifting takes place in the drawing plane of FIG. 6, in which the optical axes of the two cameras 18 and 20 are also found.

Figure 7:
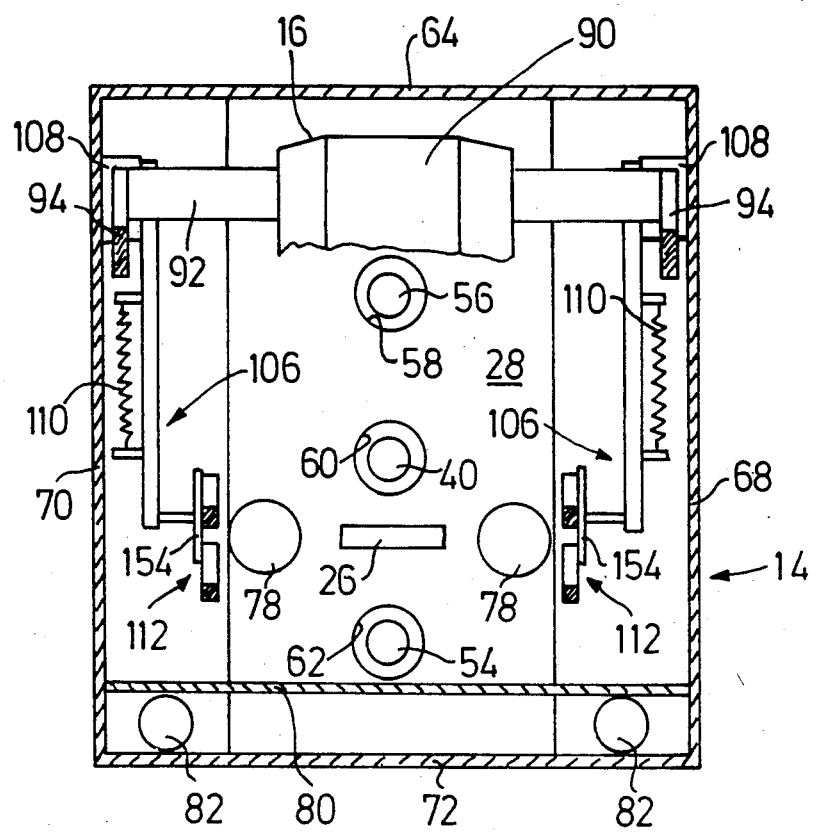
FIG. 7 a transverse view along C - D in FIG. 6.
Figure 8:
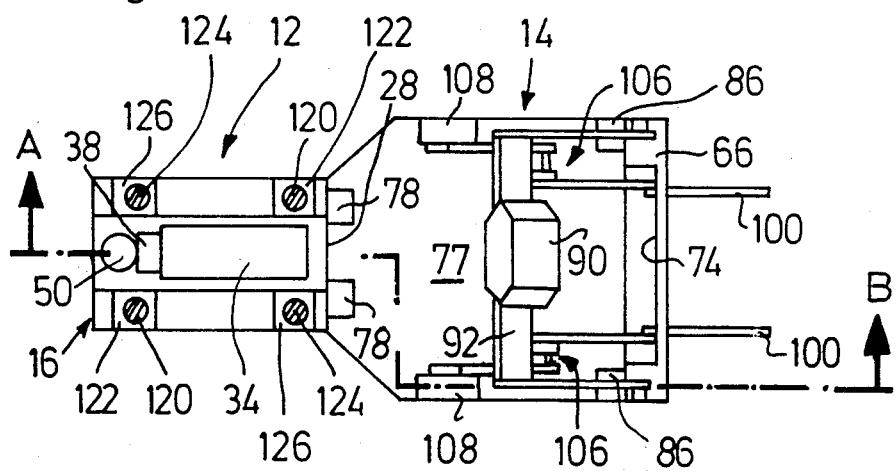
FIG. 8 a top-view in reduction to FIG. 6, whereby the upper walls of the camera unit of the optical head according to FIG. 6 are removed.

As may be seen in FIGS. 6 and 7, the level front wall 28 of the apparatus carrier 16 has three apertures 58, 60 and 62, which are located in the middle of the front wall 28 vertical to one another. Behind the aperture 58 the objective 56 of the upper camera 20 is situated, behind the aperture 60 the objective 40 of the projector 22 is situated and behind the aperture 42 the objective 54 of the lower camera 18 is situated. The apertures 58, 60 and 62 are dimensioned in such a manner that they do not impair the viewing ranges of the two cameras and the projector, respectively.

In the middle between the two apertures 60 and 62 the front wall 28 has an additional aperture in which the lens arrangment 26 is fixed. The lens arrangement 26 and the observation object 24 are situated in the optical head 12 and shaped in such a manner that at the point when the human head 8 comes into its measuring position, the person will see the observation object 24 by means of the lens arrangement 26 in infinity or in at least such a great distance that a fixation of the eyes of the person on a closer point is averted.

The chamber unit 14 is permanently linked to the optical head 12. Belonging to this are a hood formed by an upper wall 14 connecting to the upper wall 30 of the apparatus carrier 16, a front wall situated on the right as seen in FIG. 6, two side walls 68 and 70 and a bottom wall 72. A large aperture 74 is formed in the front wall with a size of such proportions that with the human head 8 in the measuring position all regions of it that are intended to be picked up by the cameras 18 and 20 will be in sight of them. The hood that is formed in the manner described above envelops a chamber 77 and darkens the space between the front wall 28 of the apparatus carrier 16 and the front wall 66 and the measuring object, so that the measurement is not affected by any intrusive light. The front wall 66 is located close by the working plane 52 and has a frame 76 encircling the aperture 74, which frame 76 is made of a soft plastic material such as will prevent any sort of injury to the human head head 8 if there should be any inadvertent contact between the head and the chamber unit 14.

Within the chamber 77 lamps 78 are located on the front wall 28 of the apparatus carrier 16 on either side of the lens arrangement 26, which lamps serve the purpose of illuminating the human head located in the working plane from the front, so that they go together to form an illumination device. In addition to this illumination facility the device is equipped with an arrangement for illuminating the eye sockets. The latter as shown in the embodiment illustrated is comprised of two sources of light 82 situated below an intermediary floor 80 of the chamber unit 14. Each of the two light sources 82 emits a beam of light toward the right as seen in FIG. 6, which beam strikes a mirror 84, which deflects the light beam diagonally upward and directs it through an aperture 86 in the intermediary floor 80 onto the eye sockets of the human head postured in the measuring position. In the embodiment described one source of light 82, one mirror 84 and one aperture 86 apiece are provided for each of the two eye sockets. Through illuminating the eye sockets by means of the eye socket illumination fixture described in the above a disruptive casting of shadows can be prevented in taking certain measurements and photographs.

The device is furthermore equipped with a distance measuring instrument, which serves to ascertain when the measuring object has reached the required distance from the optical head 12, i.e., whether the measuring object has reached the measuring position. In the embodiment depicted this distance measuring instrument is comprised of two light barriers, each having an opto-electronic receiver and a transmitter assigned to it, whereby the two light barriers extend essentially horizontally at right angles to the optical axes of the cameras 18 and 20. Only one receiver 88 can be seen in FIG. 6 of the above-mentioned opto-electronic receivers and transmitters; this receiver is located in the frame 76 and thus is supported by the hood of the chamber unit 14. To the right of the receiver 88 an additional receiver is installed in the frame 76, but this additional receiver is covered in FIG. 6 by the human head 8, i.e. by the root of the nose of this head. Two transmitters assigned to these receivers are situated vertically opposite to the receivers in the drawing plane of FIG. 6 and are also installed in the frame 76 and thus supported by the hood of the chamber unit 14. Each pair consisting of an opto-electronic receiver and transmitter forms a light barrier, whereby the locations of these light barriers has been determined in such a manner that at the point when one of the two light barriers is interrupted by the measuring object, but the other is not, the measuring object will assume its measuring position. Not shown in the illustrations are the electrical connections nor the evaluation circuitry of the distance measuring instrument under description.

A calibrating object 90 is installed in the chamber 77, which object has a certain form known in the art and is used for the purpose of obtaining the data required for the calibration of the entire device. Since the photogrammetrical measuring process is not an object of the present invention, the actual calibration is not discussed here at any greater length.

The calibrating object 90 is attached to a U-shaped stirrup 92, which has two shanks 94 that are pivotally supported at their free ends on the side walls 68 and 70 of the hood. The calibrating object 90 can be moved between a rest position shown in FIG. 6, where it does not impede the free view of the two cameras 18 and 20 and of the projector 22 to the measuring object, and a calibrating position, in which the measuring object 90 is situated in the working plane. Detents 96 located on the front wall 66 of the hood serve for positioning the calibrating object 90 exactly. The calibrating object 90 is under spring tension both in its rest position and in its calibrating position, which tension is applied by a spring 98 on the stirrup 92.

The calibrating object 90 has several even surfaces, which have differing directions in space from one another and are provided with calibrating marks. One of the even surfaces of the calibrating object 90 in its calibrating position faces the camera device and during calibration will preferably be directed exactly vertically (i.e. toward the center of the earth), so that by virtue of the calibrating object in its calibrating position an absolute alignment in space of the calibrating object independent of the device will be given.

Although the calibrating object in the embodiment described will be preferably accommodated always directly or indirectly on the optical head 12, it can also be detachable from this, for example, and hooked in position solely for the purpose of calibrating on the optical head 12 and chamber unit 14, but otherwise detached from the apparatus carrier 16.

In FIG. 6 an ear scanner 100 can be seen, specifically the ear scanner for the left ear of the subject. This ear scanner has a segment 148 extending essentially horizontally as well as a segment 102 curving up from the right end of the first segment 100 in the form of a crescent, which is composed of a soft, material and is shaped to fit the outline approximately of the area between the ear and the skull of a human being. This soft segment 102 is permanently connected at its upper end to the horizontal segment 148 of the ear scanner, and at its lower end is supported by a more rigid segment 104 also in the shape of a crescent, which is not intended to come into contact with the ear or skull. The ear scanner 100 just described is connected in hinge form with a parallel guiding instrument 106, which in the embodiment depicted consists of two parallelogram guides 112 and 150 coupled with one another, whereby one end of the parallel guide device 106 is secured to the side wall 70 by means of a block 108. The upper parallelogram guide 150 is comprised of two struts 152 extending parallel to one another, which at their upper end are hinged to the block 108 so as to be pivoted. The two lower ends of the struts 152 are connected in the form of a hinge to a plate 154, whereby the four articulated points of the two struts 152 are situated at the corners of a parallelogram. The lower parallelogram guide 112 is also comprised of two struts 156 that run parallel to one another and that at their one end are hinged to the plate 154 and at their other end are connected in hinge form to the ear scanner 100; the four articulated points of the struts 156 are also situated at the corners of a parallelogram. In consideration of the fact that the ear scanner is intended to be moved in and out of the chamber unit 14 essentially horizontally, the upper parallogram guide 150 will preferably be located in such a manner that the struts 152 extend essentially vertically while forming a rectangle, as opposed to the struts 156 of the lower parallogram guide 112, which will preferably form a rectangle when they are extended essentially horizontally. An ear scanner 100 and a parallel guiding instrument as described in the above for the left ear are also provided for the right ear, as may be seen in FIG. 7, whereby the two ear scanners and the two parallel guiding instruments are patterned symmetrically to one another. Each parallel guiding instrument 106 is equipped with a spring 110 that tends to pull each respective ear scanner 100 to the left as seen in FIG. 6. The parallel guiding device 106 makes it possible for each respective ear scanner 100 to be shifted parallel to itself upward and downward as well as forward and backward, i.e. to the left and to the right as seen in FIG. 6, and in this manner to stay in contact with the furrow between the auricle and the skull. Each ear scanner is provided with markings, of which only three are shown in FIG. 9, which markings are visible to the two cameras 18 and 20 and which with the ear scanners 100 placed on the ears of the head coming into the measuring position are situated approximately in the working plane 52. The markings 114, together with the pattern picture projected onto the face, are picked up by the two cameras 18 and 20, which join to form the camera equipment of the device; this makes it possible to ascertain the position and alignment of the ear scanner 100 in space and thus to determine the transition area between the ear and the skull with the use of the pictures. The hinges of the lower parallelogram guide 106 will preferably be in the form of a ball-and-socket joint, so that the ear scanner within certain limits can also execute a rotation around the longitudinal axis of its straight segment extending essentially horizontally.

In the embodiment described in the above the parallel guiding instruments 106 of the two ear scanners 100 are mounted on the chamber unit 14 and thus directly on the apparatus carrier 16 of the optical head 12. However, the two parallel guiding instruments can also be installed on the seating facility 6 and preferably on the head rest 10 of it, in which case the ear scanners 100 will then be applied to and pressed against the ears, instead of the ear scanners being pushed forward by their parallel guiding instruments 106, as is the case in the embodiment illustrated.

As will be seen from the above description, the optical head 12 and the chamber unit 1 can be moved jointly in a vertical direction relative to the base 2 permanently fixed to the device and also in the horizontal direction defined by the optical axes of the cameras 18 and 20. For this purpose a sliding carriage is located in the base 2 (not shown in the illustration), which carriage travels in the stated horizontal direction and to which an electric motor, also not shown, is assigned. A slot 116 is formed on the upper side of the base 2, in the direction of which slot and below which the carriage (not shown) can be moved. The open region of the slot is covered over with a louver 128. The sliding carriage (not depicted) carries a guiding device to guide the apparatus carrier 16 on the carriage in its vertical direction. Of this guiding device only two vertical guide bars 120 are visible in FIG. 8, and these are mounted on the sliding carriage (not shown) and are run on guide boxes 122, which are attached to the apparatus carrier 16, and specifically in the region of two diagonally opposite edges of the quadrilateral apparatus carrier. Parallel to the two remaining edges run two drive spindles 124, which are set so are to be rotatable in the sliding carriage (not shown) and are supported axially to the latter. The two drive spindles 124 are each engaged in a nut 126, which is attached to the apparatus carrier 16. To both drive spindles an elecmotor driving device (not shown) is assigned, with the aid of which the drive spindles can be rotated in order to drive the optical head 12, together with the chamber unit 14 in this manner upward or downward. The guide bars 120 and the drive spindles 124 are enveloped below the optical head 12 by a telescopic cover 128.

Not described or illustrated in the above are the electrical connections and the control devices of the cameras 18 and 20, of the projector 22, of the light barriers, of the various electric motor driving devices, as well as the placing drives 46 and 50 since these electrical connections and control devices are not necessary for the understanding of the invention.

The above described device operates in the following manner. A person, whose face is to be measured, takes a seat in the seating facility 6 and is requested to assume a comfortable, upright posture while keeping the head essentially straight up and straight forward, i.e., to look into the aperture 74. After the person has confirmed that he has assumed this position, the head rest 10 is applied to the head 8 from behind so that it will be easier for the subject to keep the head 8 in the position thus assumed. Following this, the electric motor placing drives for the horizontal movement and vertical movement of the optical head 12 are activated by means of a control device (not shown in the illustration) in such a manner that the optical head 12 is traveled horizontally and/or vertically until the head has assumed its measuring position. At a point when the interval of the human head 8 is still greater from optical head 12 than in the measuring position, an arrow-shaped picture of a marker 130 will already be seen on the monitor arrangement (not illustrated), on which the pictures taken by the two cameras 18 and 20 will be reproduced; the pattern of the arrow-shaped marker will preferably be located on the diapositive 42 in such a manner that it is situated on the optical axis of the objective 40 of the projector 22. The optical head 12 is then moved up to such a height that the marker image 130 is projected at the height of the root of the nose onto the bridge of the nose, as is shown in FIG. 9. At this point or immediately prior to it, the two ear scanners 100 are moved out of the chamber 77 in which they had previously been stored far enough for the soft segments 102 can be applied from behind into the furrow between the auricle and the skull with slight pressure. Following this, the optical head 12 is moved further toward the measuring position and face until the face has assumed its measuring position. When the measuring position has been reached, the distance measuring device in the form of the two light barriers reacts, whereupon the forward motion of the optical head 12, together with the chamber unit 14, is stopped, either manually or automatically. In the event it should be necessary, a correction of the vertical position of the optical head 12 will be made once more, till the the marker image 130 is at the desired height as described in the above. With the use of the placing drive 50 the projector 22 is then rotated on its axis 48 until the marker image 130 lies centrally on the bridge of the nose, unless this was previously the case. Finally, the diapositive 42 is turned until a reference line of the pattern picture 44 is in its nominal position, for example, until it touches the outer edge of the irises of both eyes, as shown in FIG. 9. When the condition illustrated in FIG. 9 is ultimately attained, the two pictures can simultaneously be made by means of the camera equipment consisting of the two cameras 18 and 20, which pictures are then subjected to photogrammetrical evaluation. Without the use of the projected pattern image 44 and the projected marker image 130, and with the ear scanners 100 removed and the lamps 78 turned on, a further shot of the face can be made to afford a comparative photograph, by using the camera 18, for example.

After the desired pictures have been taken, the optical head 12 and the chamber unit 14 are moved away from the human head 8, and returned, if desired, to the rest position with respect to the base 2.

In the above-described embodiment the cross-positioning is accomplished by pivoting the projector on the axis 48. It will be understood that this cross-positioning can also be accomplished solely or additionally by having the optical head 12, together with the chamber unit 14, travel in a second horizontal direction relative to the base 2 permanently connected to the device, which direction will extend vertically to the first horizontal direction. In the embodiment described in the above the vertical positioning is accomplished exclusively by moving the optical head 12 in a vertical direction. Alternatively, provision could also be made for the pattern image 44 and the marker image 130 in FIG. 9 to be shifted in a vertical direction by a corresponding motion of the projector 22 as well as the diapositive 42. Finally, it would also be possible to turn the entire projector 22 on the optical axis of its objective 40, instead of to turn the diapositive 42 in the projector 22.

The second embodiment of the device as shown in FIGS. 3, 4 and 5 does not differ from the preferred embodiment described above with respect to the design of the optical head 12 and the chamber unit 14, for which reason the explanations with regard to it will not be repeated anew. In the embodiment according to the FIGS. 3 through 5 two vertical columns 132 and 134 are attached to the platter-shaped base 2, which columns are connected at their upper ends to one another via a yoke 136. A sliding carriage 138 traveling vertically is guided in the columns 132 and 143, and this is driven in its vertical movements by means of an electric motor driving device (not shown). The sliding carriage 138 supports the optical head 12 in such a manner that the apparatus carrier 16 of the optical head 12 is movable on the sliding carriage 138 in the first horizontal direction, this movement being effected by means of an electric motor driving device not shown in the illustration.

Figure 10:
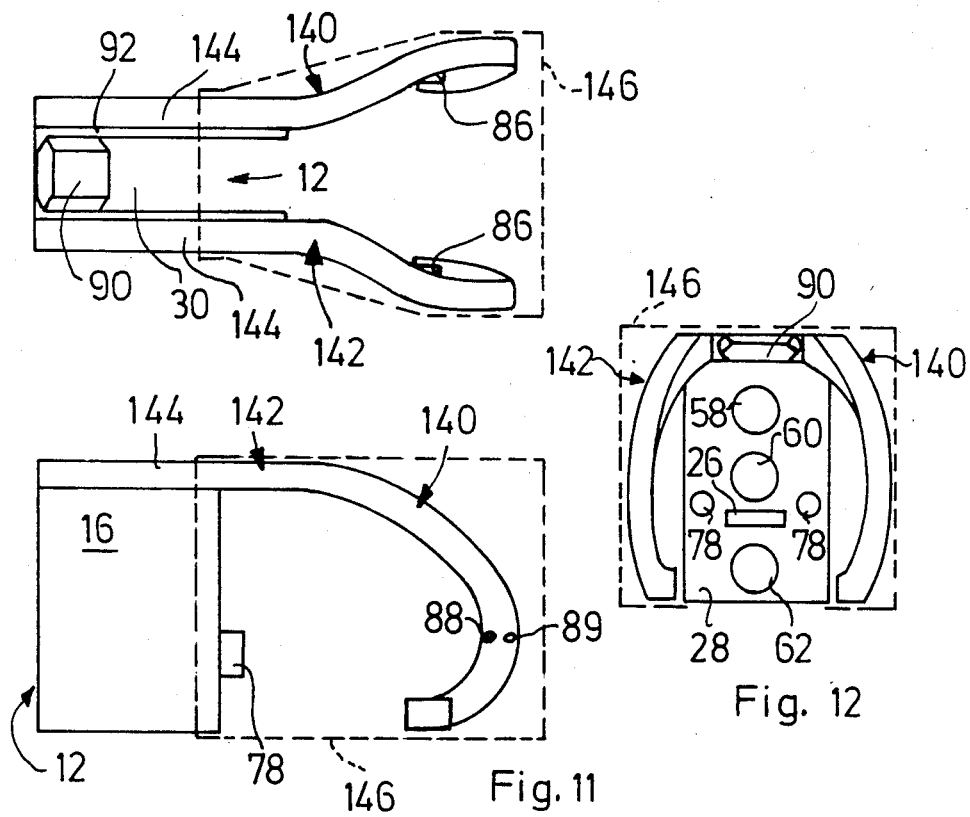
FIG. 10 a top-view of essential parts of a third embodiment of the device.

The third embodiment as shown in FIGS. 10, 11 and 12 differs from the preferred embodiment essentially through the fact that the chamber unit 14 of the preferred embodiment is not found here. The optical head 12 of the third embodiment has the same design as the optical heads of the preferred and second embodiments, for which reason this will not be explained anew here. The optical head 12 of the third embodiment can be connected to the base either as in the preferred embodiment or as in the second embodiment and supported by it. The base and the fixtures connecting the optical head 12 with the base are shown depicted for the third embodiment. The parallel guiding devices of the ear scanners are installed in the seating facility not shown in FIGS. 10, 11 and 12.

In the embodiment in accordance with FIGS. 10 through 12 an arm 140 is attached to the upper wall 30 of the apparatus carrier 16, together with a second arm 142. As shown in FIGS. 10 and 12, the two arms 140 and 142 are designed symmetrically to the longitudinal median plane of the optical head 12. Each of the two arms has a straight segment 144 attached directly to the apparatus carrier, and on the two segments 144 is attached the stirrup 92 so as to be movable with the calibrating object 90. Curving downward and slightly to the outside, each arm 140 extends from the segment 144 outward to the locations of the transmitters and receivers of the light barriers constituting the distance measuring device; in FIG. 11 the receiver 89 aligned with the receiver 88 is also visible, because in FIG. 11 it is not covered by the human head 8. The transmitters assigned at the places appropriate to the receivers 88 and 89 are located in the arm 142.

The two arms 140 and 142 extend below the transmitter and receiver of the light barriers in the shape of an arc in the direction toward the optical head 12 and ultimately manifest an open end. Near these open ends the elements of the eye socket illumination fixture are situated in the arms 140 and 142, of which only the apertures 86 can be seen in FIG. 10.

The embodiment according to FIGS. 10 through 12 has the advantage of not irritating the subject whose head is to be measured by virtue of the relatively large chamber unit 14 with its dark aperture 74 as in the preferred embodiment during the time the optical head 12 and the chamber unit 14 are being moved forward. The embodiment according to FIGS. 10 through 12 is especially well-suited to instances in which care has been taken for the lighting conditions in the room where the device is set up to be such that the photogrammetry is not affected by instrusive light. In addition to this, a cover 146 (shown in broken lines) can be provided for this embodiment in approximately the same shape as the hood in the preferred embodiment, which cover will also provide for darkening the interior. The cover 146 can be put on and taken off in a simple fashion and will come into use when the above-stated requirement with respect to intrusive light is not fulfilled.

The mode of operation of the second and third embodiments of the present device coincide with the mode of operation of the preferred embodiment, for which reason they are not described anew.

It will be understood that numerous variants of the above-described embodiments are possible without exceeding the bounds of the present invention.

The present device for the photogrammetrical measurement of the human head, especially of the middle region of the face with the eye sockets, the nose, the cheek bones and the brows, is comprised of a projector for projecting a pattern image onto the face and two cameras which can simultaneously take two pictures from two different directions of the face and head with the pattern image projected on t. The two cameras and the projector are supported by an apparatus carrier, which can be moved in a vertical direction relative to a base permanently connected to the device and in at least one horizontal direction. This minimum of one direction coincides with the optical axes of the cameras. The device will facilitate bringing both the projector and cameras on the one hand and the human head on the other into the required relative position to one another as necessary to take the pictures.

We claim:

1. Apparatus for photogrammetrically measuring the human head, comprising: base means; projector means for projecting a pattern image onto the head; camera means capable of simultaneously taking at least two pictures of the head with the pattern image projected onto it; and an apparatus carrier affixed to said base means and carrying both said camera means and said projector means, said apparatus carrier firstly being moveable relative to said base means in a vertical direction and secondly being moveable relative to the head to be measured in a horizontal direction essentially parallel with an optical axis of the camera means.

2. The apparatus of claim 1, wherein said apparatus carrier is mounted for movement relative to said base means in a second horizontal direction essentially normal to the first horizontal direction.

3. The apparatus of claim 1, further comprising a sliding carriage mounted on said base means for movement relative to said base means in a first horizontal direction essentially parallel with an optical axis of the camera means, said apparatus carrier being supported on said carriage.

4. The apparatus of claim 3, further comprising at least one vertically extending drive spindle supported on the sliding carriage, said spindle being engaged with a nut fixed on the apparatus carrier, and means for guiding the vertical movement of said apparatus carrier with respect to the sliding carriage.

5. The apparatus of claim 1, further comprising a vertical column rigidly attached to the base and a sliding carriage mounted on said column for vertical movement with respect to said column, said apparatus carrier being mounted on said sliding carriage for movement in said first horizontal direction.

6. The apparatus of any one of claims 1 through 5, further comprising an electric motor and drive means for moving said apparatus carrier in the directions of movement possible for it.

7. The apparatus of any one of claims 1 through 5, further comprising means mounted on said apparatus carrier for measuring the distance of the human head from the camera means and the projector means.

8. The apparatus of claim 7 wherein said means for measuring distance comprises two light barriers, each including an optoelectronic receiver and a transmitter assigned to it, said two light barriers extending essentially horizontally at right angles to the optical axis of the camera means.

9. The apparatus of claim 8 further comprising an illumination fixture installed on the apparatus carrier for illuminating the head essentially from the front.

10. The apparatus of claim 9, wherein said illumination fixture transmits two illuminating light rays diagonally upward to illuminate the eye sockets.

11. The apparatus of claim 10, further comprising at least one arm attached to the apparatus carrier, said arm supporting said light transmitters, said light receivers and also supporting the eye socket illumination fixture.

12. The apparatus of claim 11, further comprising a detachable cover locatable on said one arm and the apparatus carrier for darkening the space between the camera means and the projector means on the one hand and the distance measuring means on the other.

13. The apparatus of claim 8, further comprising at least one arm attached to the apparatus carrier, said arm extending to the locations of said two transmitters and two receivers and supporting the transmitters and receivers.

14. The apparatus of claim 1, wherein said projector means is pivotally mounted in the apparatus carrier whereby a pivoting of the projector means causes horizontal movement of the projected pattern image, and further comprising drive means for pivoting the projector means.

15. The apparatus of claim 14, further comprising a diapositive inserted in the projector means, said diapositive being supported for rotation in the projector means around the optical axis of the projector means and drive means for turning the diapositive.

16. The apparatus of claim 15, wherein said camera means comprises a first and a second camera, said cameras being arranged to simultaneously each take a picture of the human head from different directions with the pattern image projected on it.

17. The apparatus of claim 11, wherein one of said cameras is installed above the projector means and the other of said cameras is installed below the projector means.

18. The apparatus of claim 16, wherein each camera is a video camera.

19. The apparatus of claim 18 wherein each camera is a digital video camera.

20. The apparatus of claim 1, further comprising means for producing said two pictures in two different areas of the image plane of said camera means.

21. The apparatus of claim 1, further comprising an observation object supported by the apparatus carrier and a lens arrangement assigned to the observation object, which lens arrangement allows the observation object to appear at a great distance.

22. The apparatus of claim 1, further comprising a calibrating object and means for mounting said calibrating object on said apparatus carrier for movement between a calibrating position and a rest position assuming essentially the position of the head during measurement and, in its rest position, being located outside the viewing range of the camera means.

23. The apparatus of claim 1, further comprising two ear scanners, each of which can be applied to the area between one of the ears and the skull of the head and which are provided with markings which are visible simultaneously with the front side of the head when the ear scanners are in operative position, and means for mounting each of the ear scanners for parallel movement of said ear scanners in a vertical direction and in the first horizontal direction.

24. The apparatus of claim 23, further comprising a seating facility for the person whose head is to be measured photogrammetrically, said means for mounting said ear scanners for parallel movement being installed on the seating facility.

25. The apparatus of claim 1, further comprising a hood mounted on the apparatus carrier, said hood having an aperture for receiving the human head, said camera means and the projector means being located in said hood whereby the interior of the hood is protected from receiving ambient light when a human head is located in said aperture for measurement.

26. The apparatus of claim 24 further comprising an illumination fixture for illuminating the head essentially from the front, light barriers for measuring the distance of the head from the camera means and projector means, a calibrating object, and two ear scanners each mounted for parallel movement in a vertical direction and in the first horizontal direction, said illumination fixture, said light barriers, said calibrating object and means for moving said ear scanners each being situated on or in the hood.

* * * * *